(12) United States Patent
Keener (10) Patent No.: US 10,940,279 B2
(45) Date of Patent: Mar. 9, 2021

(54) AROMATHERAPY DEVICE

(71) Applicant: Jennifer K. Keener, Massillon, OH (US)

(72) Inventor: Jennifer K. Keener, Massillon, OH (US)

( * ) Notice: Subject to any disclaimer, the term of this patent is extended or adjusted under 35 U.S.C. 154(b) by 183 days.

(21) Appl. No.: 15/890,486

(22) Filed: Feb. 7, 2018

(65) Prior Publication Data

US 2018/0161529 A1    Jun. 14, 2018

Related U.S. Application Data

(63) Continuation-in-part of application No. 14/748,352, filed on Jun. 24, 2015, now Pat. No. 9,925,351.

(Continued)

(51) Int. Cl.
| | | |
|---|---|---|
| *A61M 15/00* | (2006.01) | |
| *A61L 9/12* | (2006.01) | |
| *A61L 9/04* | (2006.01) | |
| *A61M 15/08* | (2006.01) | |
| *A61M 21/02* | (2006.01) | |
| *A61M 16/14* | (2006.01) | |
| *A61M 21/00* | (2006.01) | |
| *A61M 11/04* | (2006.01) | |
| *A01M 1/20* | (2006.01) | |

(52) U.S. Cl.
CPC ........ *A61M 15/08* (2013.01); *A61M 15/0021* (2014.02); *A61M 16/14* (2013.01); *A61M 21/02* (2013.01); *A01M 1/2055* (2013.01); *A61L 9/048* (2013.01); *A61L 9/125* (2013.01); *A61M 11/04* (2013.01); *A61M 15/0003* (2014.02); *A61M 2021/0016* (2013.01); *A61M 2210/0618* (2013.01); *A61M 2210/0625* (2013.01)

(58) Field of Classification Search
CPC .. A61M 15/08; A61M 15/0021; A61M 16/14; A61M 21/02; A61M 15/0003; A61M 11/04; A61M 2021/0016; A61M 2210/0618; A61M 2210/0625; A61L 9/035; A61L 9/04; A61L 9/125; A61L 9/048; A01M 1/2055
USPC ..................... 120/200.23; 239/245
See application file for complete search history.

(56) References Cited

U.S. PATENT DOCUMENTS

| 168,972 A | 10/1875 | Dayton | |
| 2,620,228 A * | 12/1952 | Newell | ..................... B65F 7/00 |
| | | | 239/57 |

(Continued)

*Primary Examiner* — Joseph A Greenlund
(74) *Attorney, Agent, or Firm* — Sand, Sebolt & Wernow Co., LPA (57) ABSTRACT

An aromatherapy device may define a plurality of wells arranged in an array to be filled with fluid as scented pairs such that two adjacent wells may be positioned beneath nostrils of a user while resting a portion of the device against the upper lip. The wells may be formed in respective cylinders positioned between the portion of the device that is designed to rest against the lip. There may be a plurality of wells that face a first direction and that face an opposite second direction. The wells may be similar shaped and sized so as to receive similarly viscous fluids therein having different scents associate therewith. The viscosity of the fluids should be high enough to resist the pull of gravity and preclude the fluid from flowing out of the well when the device is positioned upside down and some of the wells are, at least temporarily, downwardly facing.

14 Claims, 7 Drawing Sheets

Related U.S. Application Data (60) Provisional application No. 62/019,612, filed on Jul. 1, 2014.

(56) References Cited

U.S. PATENT DOCUMENTS

| | | | | |
|---|---|---|---|---|
| 2,755,954 | A * | 7/1956 | Antritter | A01M 1/2055 220/4.21 |
| 3,087,679 | A * | 4/1963 | Wilson | A01M 1/205 239/57 |
| 4,118,226 | A * | 10/1978 | Bourassa | F24F 3/16 96/222 |
| 4,544,592 | A * | 10/1985 | Spector | A61L 9/03 239/56 |
| 4,762,275 | A * | 8/1988 | Herbert | A61L 9/12 239/45 |
| 4,811,731 | A * | 3/1989 | Newell | A61M 15/0045 128/203.15 |
| 4,849,606 | A * | 7/1989 | Martens | B65D 77/2024 392/390 |
| 4,890,791 | A * | 1/1990 | Hoffman | A61L 9/127 239/326 |
| 4,955,945 | A * | 9/1990 | Weick | A61M 15/0011 128/203.12 |
| 5,121,881 | A | 6/1992 | Lembeck | |
| 5,167,877 | A * | 12/1992 | Pai | A61L 9/122 261/18.1 |
| 5,485,836 | A * | 1/1996 | Lincoln | A41D 13/1176 128/206.11 |
| 5,805,768 | A * | 9/1998 | Schwartz | A61M 15/0045 261/DIG. 65 |
| 5,943,816 | A | 8/1999 | Hyatt et al. | |
| 6,126,632 | A | 10/2000 | Verbovszky et al. | |
| 6,195,933 | B1 * | 3/2001 | Woodruff | A01M 1/2011 43/131 |
| 6,557,375 | B1 * | 5/2003 | Simmons | A44C 15/002 63/1.11 |
| 6,713,024 | B1 * | 3/2004 | Arnell | A61L 9/125 239/57 |
| 7,841,337 | B2 | 11/2010 | Djupesland | |
| 8,460,609 | B1 * | 6/2013 | Wheatley | A61L 9/042 422/123 |
| 8,662,409 | B2 * | 3/2014 | Tasz | A61L 9/048 239/6 |
| 8,677,679 | B2 | 3/2014 | Black et al. | |
| 8,851,458 | B1 * | 10/2014 | Wilson | A61L 9/042 261/101 |
| 9,192,691 | B2 | 11/2015 | Bourne | |
| 9,554,595 | B2 * | 1/2017 | Buchberger | A24F 7/02 |
| 10,080,815 | B2 * | 9/2018 | Cardinal | A61L 9/125 |
| 2006/0196966 | A1 * | 9/2006 | Cheng | B65D 25/20 239/60 |
| 2008/0190935 | A1 | 8/2008 | Pankhurst et al. | |
| 2009/0212124 | A1 * | 8/2009 | Kenny | A01M 1/2044 239/58 |
| 2010/0199984 | A1 | 8/2010 | Williams, III et al. | |
| 2011/0011947 | A1 | 1/2011 | Wallis et al. | |
| 2014/0096767 | A1 * | 4/2014 | Pearson | A61M 15/0091 128/202.21 |
| 2014/0112649 | A1 | 4/2014 | Irvin et al. | |
| 2015/0048178 | A1 * | 2/2015 | Edwards | A61L 9/035 239/13 |
| 2015/0053201 | A1 | 2/2015 | Djupesland et al. | |
| 2016/0001035 | A1 * | 1/2016 | Keener | A61M 21/02 206/568 |

\* cited by examiner

AROMATHERAPY DEVICE

CROSS REFERENCE TO RELATED APPLICATIONS

This is a continuation-in-part application claiming the benefit of non-provisional U.S. application Ser. No. 14/748,352, filed Jun. 24, 2015, which claims the benefit of U.S. Provisional Application Ser. No. 62/019,612, filed on Jul. 1, 2014; the disclosure of which is incorporated herein by reference.

BACKGROUND

Technical Field

The present disclosure relates generally to the field of aromatherapy devices. More particularly, the present invention relates to aromatherapy devices including a scented fluid. Specifically, the present invention relates to a housing forming a well filled with scented fluid configured to prevent the fluid from leaking out of the housing.

Background Information

Aromatherapy is a form of treatment for certain ailments utilizing scented fluids or compounds. The scents are inhaled and a reaction occurs in the human brain to alter the user's mind, mood, cognitive abilities, or health. Some exemplary fluids often utilized in aromatherapy include essential oils, absolute oils, and carrier oils, amongst others.

One exemplary treatment which aromatherapy is used in is the cessation of cigarette smoking. When a person attempts to quit smoking cigarettes, they often have side effects such as increased hunger, which can lead to weight gain. Some aromatherapy treatments are used to reduce hunger cravings as a person weans their body from its nicotine addiction.

Recently, electronic cigarettes have begun using essential oils in their vaporizers to flavor-infuse vapor as a replacement to conventional cigarettes. The fluid for electronic cigarettes is readily available in the commercial market in a wide variety of flavors/scents and quantities.

SUMMARY

Issues continue to exist with current aromatherapy devices with the delivery of scents to a user, namely problems exist with fluid leaking out from some aromatherapy containers. Further, the electronic cigarette market keeps advancing the development of the scented fluids for use in electronic cigarettes. A need exists for an aromatherapy device configured to utilize the advantages of the wide variety of essential oils available for electronic cigarettes. The present invention addresses these and other issues.

In one aspect, an embodiment may provide an aromatherapy device comprising: a housing; a first cylinder having an inner surface, the first cylinder defining a portion of the housing; an first insert having an outer surface, the first insert smaller than the first cylinder and positioned radially inward from the inner surface; and a first aromatic fluid well formed between the inner surface of the first cylinder and the outer surface of the first insert configured to retain a scented fluid therein, wherein aroma associated with the fluid is inhaled by a user.

In another aspect, an embodiment may provide, an aromatherapy method comprising the steps of: providing a housing including a first member having an inner surface, an first insert smaller than the first member and positioned inward from the inner surface, the first insert having an outer surface, and a first aromatic fluid well formed between the inner surface of the first member and the outer surface of the first insert; filling the aromatic fluid well with a scented fluid; and positioning the housing beneath the nostrils of a user, wherein scent from the scented fluid is sensed by a user.

In yet another aspect, an embodiment may provide an aromatherapy kit comprising: a plurality of housings for retaining a scented fluid, wherein each housing includes: a first member having an inner surface; an first insert smaller than the first member and positioned radially inward from the inner surface, the first insert having an outer surface; and a first aromatic fluid well formed between the inner surface of the first member and the outer surface of the first insert configured to retain a scented fluid therein, wherein aroma associated with the fluid is sensed by a user; and a case including a plurality of retaining areas, each one of the plurality of retaining areas shaped complementary to each one of the plurality of housings, and one housing stored in one retaining area when the housing is not in use.

In one aspect, an embodiment may provide an aromatherapy device comprising: a cylindrical housing; an insert in the housing; and an aroma fluid well formed between the cylindrical housing and the insert configured to retain a scented fluid therein for inhalation of a scent by a user.

In another aspect, an embodiment may provide an aromatherapy device comprising: a scented fluid in a well formed in a housing device; and a mouthpiece coupled to the housing device positioning the fluid near a nostril of a user for inhalation of the scent.

In another aspect, an embodiment may provide an aromatherapy kit comprising: a plurality of aroma fluid containing housings; and a case including a plurality retaining areas shaped complementary to the housings for retaining the housings in the retaining areas.

In another aspect, an embodiment may provide an aromatherapy device including a housing forming two annular wells for retaining a scented fluid therein. Each well includes an insert positioned in the well to assist the retention of the fluid in the well by providing a second contact surface for the fluid to contact. The shape of the annular well and the viscosity of the fluid discourage the fluid from leaking out of the housing if laid on its side.

In another aspect, an embodiment may provide an aromatherapy device comprising: a plurality of distinct annular wells arranged in an array and spaced apart to position two adjacent and distinct annular wells from the plurality beneath two respective nostrils for inhalation of scent from fluid at least partially filling the two adjacent and distinct annular wells. This exemplary embodiment or another embodiment may further provide a first annular well longitudinally aligned with a second annular well; and a third annular well longitudinally aligned with a fourth annular well. This exemplary embodiment or another embodiment may further provide wherein the first and second annular wells are longitudinally aligned with the third and fourth annular wells. This exemplary embodiment or another embodiment may further provide wherein the first and second annular wells are transversely aligned with the third and fourth annular wells. This exemplary embodiment or another embodiment may further provide wherein the first and second annular wells are vertically aligned with the third and fourth annular wells. This exemplary embodiment or another embodiment may further provide a fifth annular well and a sixth annular well aligned transversely with the first and second annular well respectively. This exemplary embodiment or another embodiment may further provide a sixth annular well and a seventh annular well aligned longitudinally with the fifth and sixth annular wells, and transversely aligned with the third and fourth annular wells respectively. This exemplary embodiment or another embodiment may further provide eight bottom annular wells arranged in a mirrored configuration as the first through eighth annular wells. This exemplary embodiment or another embodiment may further provide a pair of longitudinally extending side members, wherein the first through fourth annular wells are disposed between the pair of side members, and a thickened dimension of the pair of side member greater than a maximum vertical dimension of the first through fourth annular wells. This exemplary embodiment or another embodiment may further provide a flat portion connected with an arcuate section, wherein the thickened dimension is measured through the flat portion. This exemplary embodiment or another embodiment may further provide a central portion extending transversely between the pair of side members. This exemplary embodiment or another embodiment may further provide a first cylinder carried by the central portion and defining the first annular well; a second cylinder carried by the central portion and defining the second annular well; a third cylinder carried by the central portion and defining the third annular well; and a fourth cylinder carried by the central portion and defining the fourth annular well. This exemplary embodiment or another embodiment may further provide a first gap defined between the first cylinder and the second cylinder, wherein the dimension of the first gap approximates a distance between the nostrils. This exemplary embodiment or another embodiment may further provide a fifth cylinder carried by the central portion and defining a fifth annular well; a sixth cylinder carried by the central portion and defining a sixth annular well; a seventh cylinder carried by the central portion and defining a seventh annular well; and an eighth cylinder carried by the central portion and defining an eight annular well.

In yet another aspect, an exemplary embodiment of the present disclosure may provide an aromatherapy device that may define a plurality of wells arranged in an array to be filled with fluid as scented pairs such that two adjacent wells may be positioned beneath nostrils of a user while resting a portion of the device against the upper lip. The wells may be formed in respective cylinders or cylindrical walls positioned between the portion of the device that is designed to rest against the lip. There may be a plurality of wells that face a first direction and that face an opposite second direction. The wells may be similar shaped and sized so as to receive similarly viscous fluids therein having different scents associate therewith. The viscosity of the fluids should be high enough to resist the pull of gravity and preclude the fluid from flowing out of the well when the device is positioned upside down and some of the wells are, at least temporarily, downwardly facing.

BRIEF DESCRIPTION OF THE SEVERAL VIEWS OF THE DRAWINGS

A sample embodiment of the invention, illustrative of the best mode in which Applicant contemplates applying the principles, is set forth in the following description, is shown in the drawings and is particularly and distinctly pointed out and set forth in the appended claims. The accompanying drawings, which are incorporated in and constitute a part of the specification, illustrate various example methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

Similar numbers refer to similar parts throughout the drawings.

DETAILED DESCRIPTION

Figure 4:
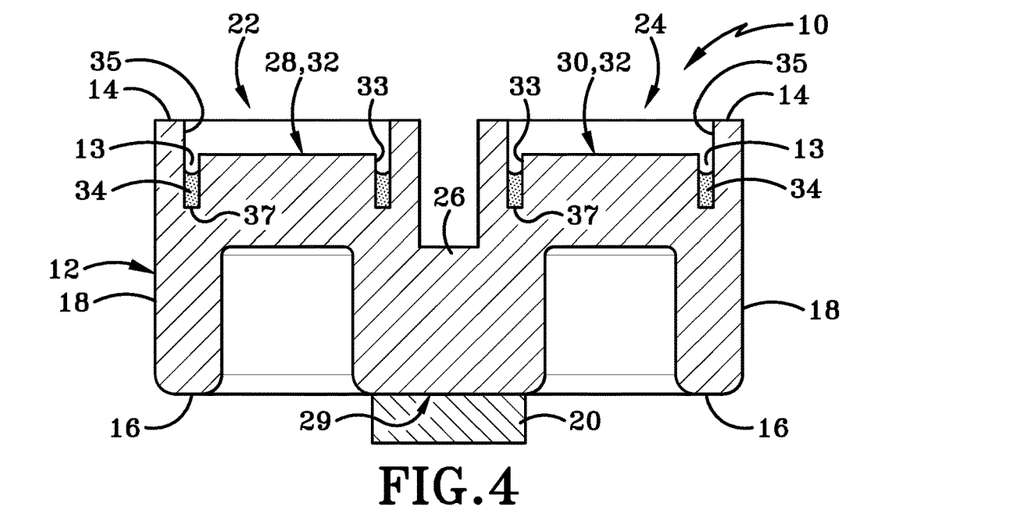
FIG. 4 is a cross-section view of the aromatherapy device taken along line 4-4 in FIG. 3.
Figure 5:
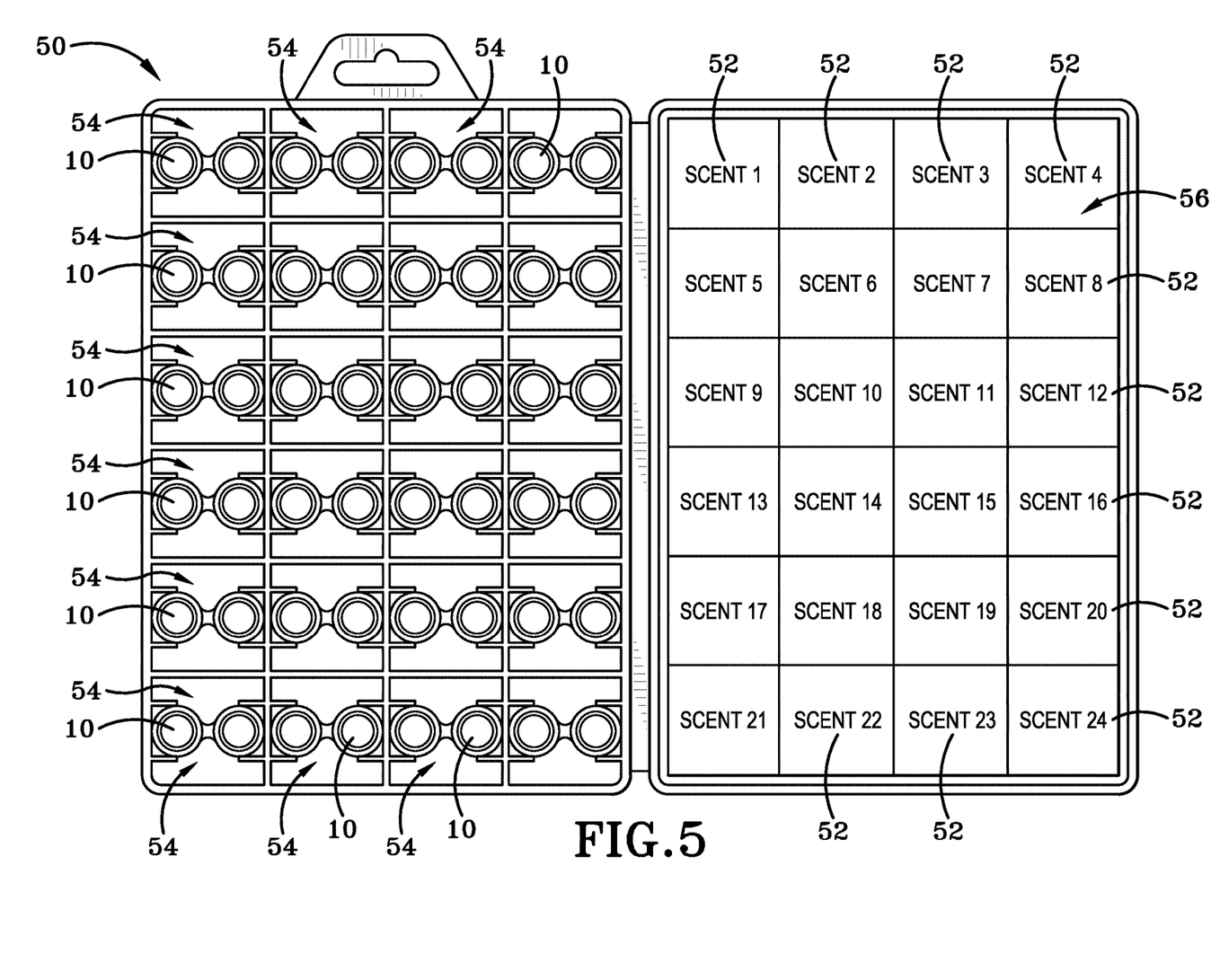
FIG. 5 is a top view of the aromatherapy device shown in a kit with a plurality of aromatherapy devices, each containing a different scent.
Figure 6:
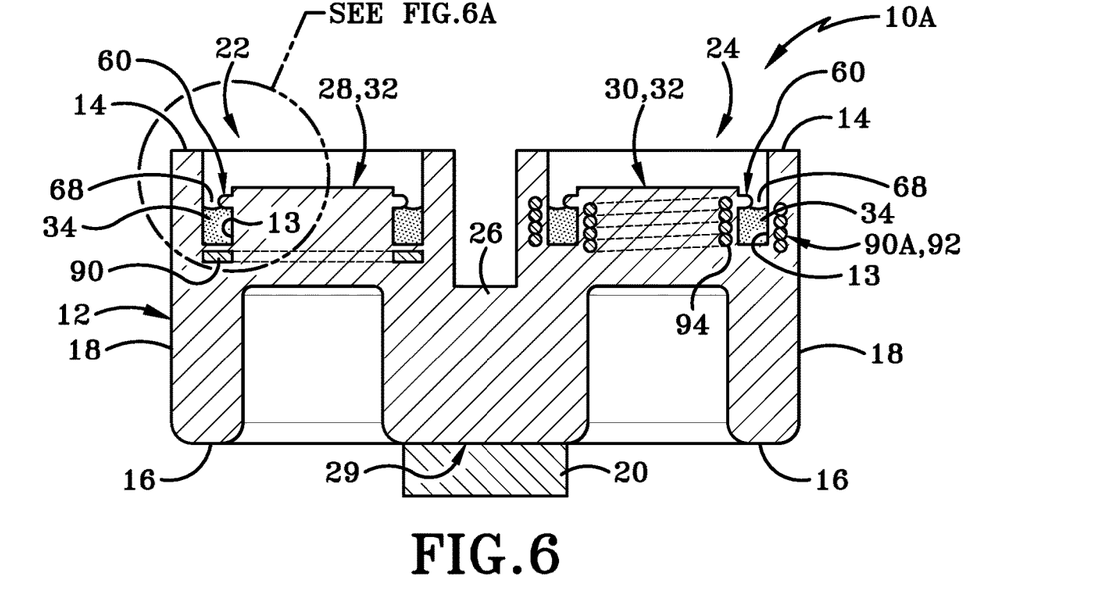
FIG. 6 is a cross-section view of the an additional embodiment of an aromatherapy device including a lip disposed in a well taken along line 4-4 in FIG. 3.
Figure 6A:
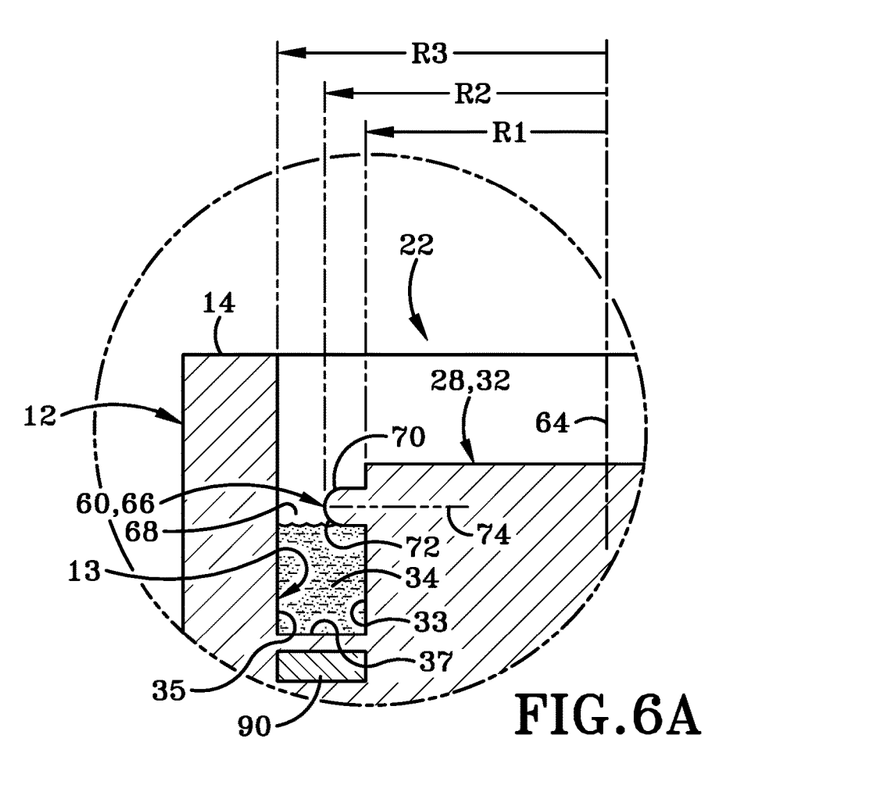
FIG. 6A is an enlarged view of the area identified in FIG. 6.

The aromatherapy device of the present invention is depicted throughout FIGS. 1-5, generally as reference numeral 10; and depicted in FIG. 6 and FIG. 6A as reference numeral 10A. Devices 10 and 10A include a housing 12 forming a pair of annular wells 13 (FIG. 3) therein for retaining an aromatherapy fluid 34 having a scent.

Figure 1:
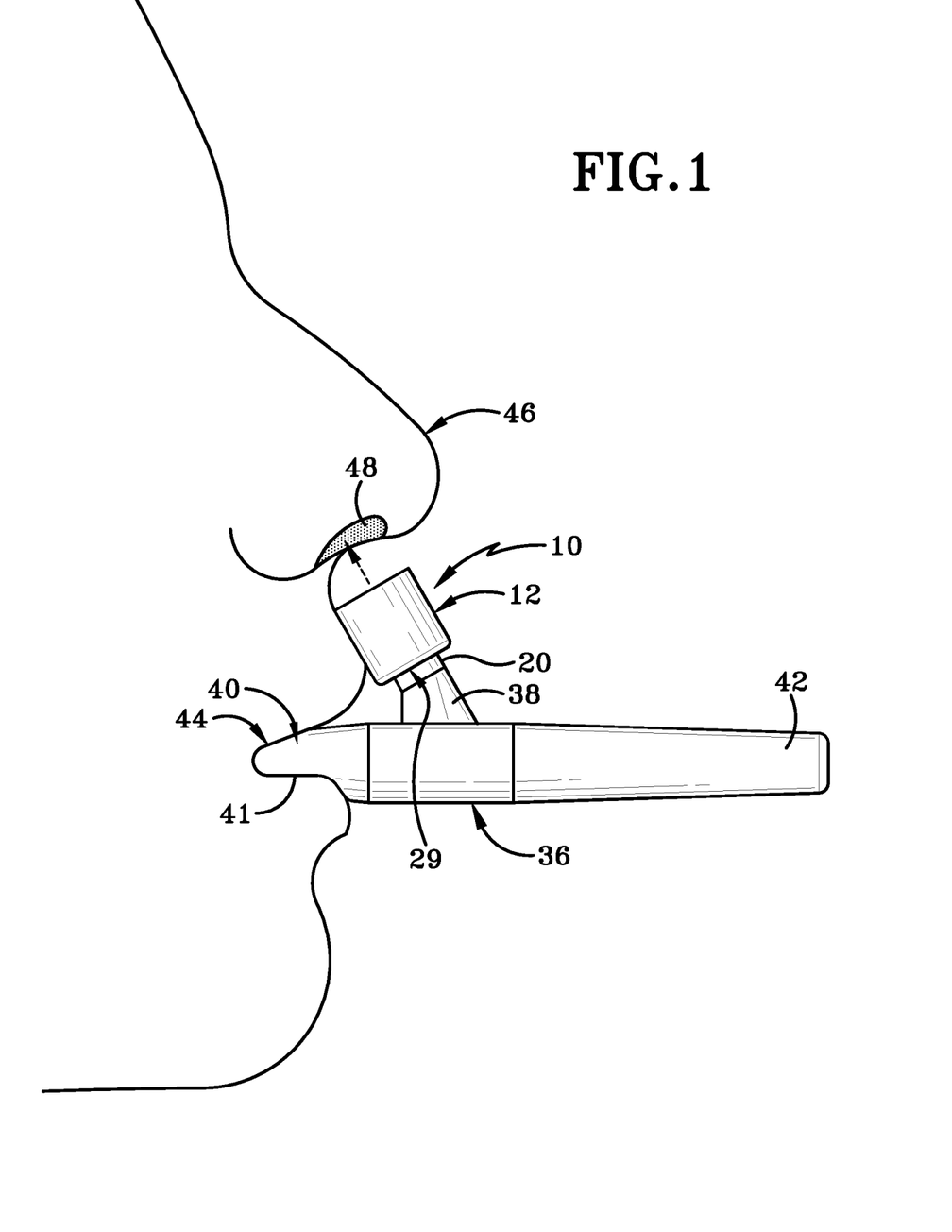
FIG. 1 is an environmental side view of the aromatherapy device of the present invention shown attached to a mouthpiece and aromas being inhaled from the aromatherapy device.
Figure 2:
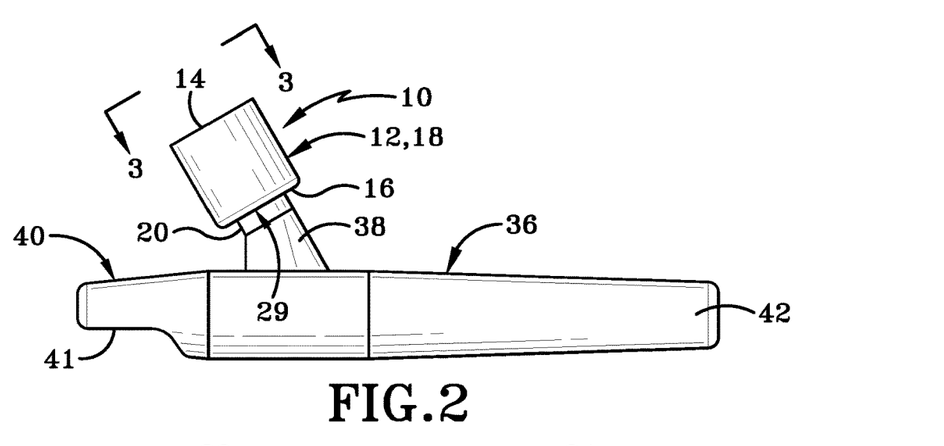
FIG. 2 is a side view of the aromatherapy device attached to the mouthpiece.

As depicted in FIG. 1 and FIG. 2, aromatherapy device 10 (or device 10A) is configured to attach a mouthpiece 36 via a connecting member 38 adjacent the attachment base 29 of housing 12. In the shown embodiment, the connecting member 38 is a magnet to connect device 10 to mouthpiece 36, however other conventional manners of mechanical, chemical, or non-mechanical and non-chemical securements in which an aromatherapy device may be coupled to a mouthpiece or handle as understood in the art are entirely possible. In one particular embodiment, connecting member 38 provides an angled connection between the housing 12 and the mouthpiece 36, wherein when the housing 12 and mouth piece 36 are connected by the angled connection, the first top surface 14 of the first cylinder is not facing directly vertical, and a limiting member (i.e., lip 60) discourages the fluid 34 from flowing out of the well 13.

Mouthpiece 36 includes a first end 40 for inserting into user's mouth 44 and a second end 42 spaced opposite therefrom for gripping with the user's hand. When the mouthpiece 36 is inserted into the user's mouth 44, device 10 (or device 10A) is aligned with the user's nose 46. In one particular embodiment, left and right annular wells 13 (introduced below) are each respectively aligned with the left and right nostril 48 of the user, maximizing the amount of scent sent by the operator during inhalation. Additionally, while reference is made to inserting an end of mouthpiece 36 into a user's mouth 44, some embodiments of mouthpiece 36 may include a recession 41 shaped complementary to a user's lip to rest thereon when in use.

Figure 3:
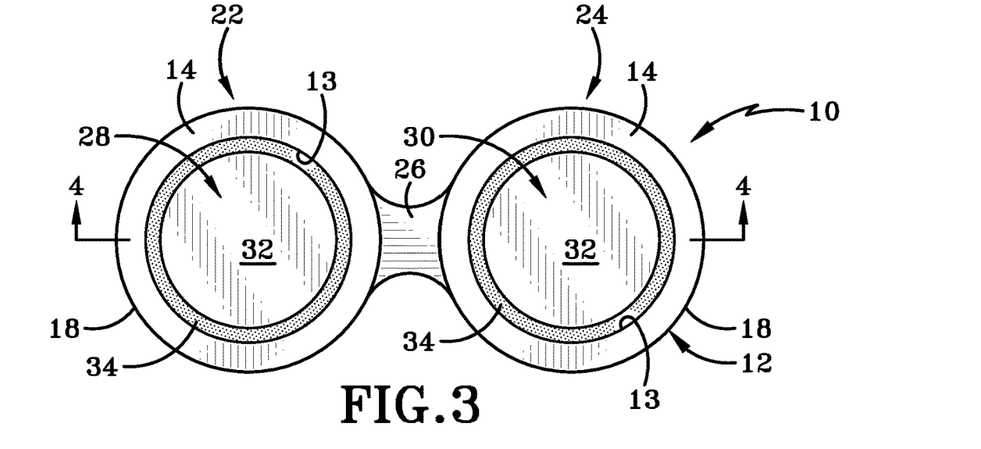
FIG. 3 is a top view of the aromatherapy device taken along line 3-3 in FIG. 2.

As detailed in FIGS. 2-4, housing 12 includes an upwardly facing top surface 14 spaced apart from a downwardly facing bottom surface 16 and a sidewall 18 extending therebetween. Sidewall 18 is substantially continuous and curvilinear having a generally figure-eight-like configuration when viewed from above (FIG. 3). Housing 12 further includes an attachment member 20 near a base 29 on or adjacent the bottom surface 16.

Each annular well 13 is formed in respective left and right end cylinders 22, 24 of the figure eight housing 12. Left and right cylinders 22, 24 are connected to each other via a middle connection member 26. A first insert 28 and a second insert 30, each including an annular outer surface 33, respectively bounds a portion of each annular well 13. An inner surface 35 on each left and right cylinder 22, 24 bounds annular well 13 opposite annular surface 33. Annular surface 33 faces inner surface 35 when viewed in cross section.

With primary reference to FIG. 4, first and second inserts 28, 30 have a top surface 32 lower than the top surface 14 of housing 12 which is configured to act as a retaining edge for the aroma fluid filled within each well. One non-limiting advantage of the inserts 28, 30 is that it retains a viscous scented fluid 34 in the well by providing another surface for the viscous fluid 34 to contact.

Well 13 has a depth measured from top surface 32 to a well bottom 37. In one embodiment, the well depth may be in a range from about 1, 2, or 3 millimeter (mm) to about 9, 10, or 11 mm. Further, in device 10, well 13 has a uniform width in cross section. Stated otherwise, the width of well 13 is the same at the top of the well as it is near the bottom of the well. The width of well 13 measured from annular surface 33 to inner surface 25 may be in a range from about 0.1, 0.25, or 0.5 mm to about 1, 2, or 3 mm.

With reference to the viscous aromatherapy fluid 34 retained in annular wells 13 on device 10, one exemplary non-limiting aroma fluid 34 is commercially available as an E-Liquid for electronic cigarettes for sale by Vapor4Life Inc. of 4100 Commercial Ave, Northbrook, Ill. 60062. In one particular embodiment, fluid 34 contains an amount of glycerin, propylene glycol, or mixture thereof to create a viscosity that discourages the fluid 34 from leaving the well 13 or flowing out of the well 13 under gravitational forces even when housing 12 is resting along the sidewall 18 on its side. In one particular embodiment, fluid 34 may be a non-Newtonian fluid.

Fluid 34 may be fabricated to include various scents from scent additives. Some non-limiting exemplary scents associated with viscous fluid 34 are chocolate peppermint, peanut butter cup, pancake, waffle, clove, chocolate, vanilla, cinnamon roll, caramel, English toffee, Choco-caramel peanut, peppermint ice cream, milk chocolate macadamia nut, white chocolate, blueberry/peach cobbler, chocolate-covered banana, almond coconut, coffee, expresso coffee, caramel mocha frappe, café mocha, vanilla mocha frappe, cappuccino, vanilla shake, champagne, java mint, rum and cola, Irish cream, energy drink, blueberry, peach, grape, cherry, regular tobacco, menthol tobacco, pipe tobacco, and cigar tobacco.

Scented fluid 34 provides an aroma-based therapeutic effect when the aroma associated with scented fluid 34 is inhaled by a user. In another particular example, fluid 34 to be inhaled may have cognitive altering abilities, such as to relieve stress and improving the mood of the user.

As depicted in FIG. 5, in one particular embodiment of the present invention, device 10 or device 10A is supplied as part of a kit 50 with a plurality of scents 52, each distinct from the other scents (exemplary scents provided above) for home use, enabling a user to sense a wide variety of smells. The kit 50 includes a plurality of device retention areas 54 configured to securely store a plurality of devices 10 or a plurality of devices 10A in a safe environment. The kit 50 may retain the devices 10, 10A in a manner such that the top surface 14 of housing 12 faces upward, or alternatively, kit 50 may store devices 10, 10A on their side. In each configuration, aroma fluid 34 should not leak out from the top of the annular well 13. In accordance with one particular embodiment of the present invention, housing 12 is constructed from a durable material, such as metal or a polymer that is resistant to breakdown from any chemicals residing in the fluid. Further, kit 50 includes an index 56 on the inside lid to assist a user in locating a specific scent pre-loaded in a corresponding housing. While FIG. 5 depicts a total of twenty four non-limiting scents, clearly there may be a different number of scents depending on the size of the kit.

In one exemplary embodiment, aromatherapy kit 50 comprises: a plurality of devices 10 for retaining a scented fluid, wherein each device 10 includes: a first member having an inner surface 35; an first insert 28 smaller than the first member and positioned radially inward from the inner surface 35, the first insert 28 having an outer surface 33; and a first aromatic fluid well 13 formed between the inner surface 35 of the first member and the outer surface 33 of the first insert configured to retain a scented fluid 34 therein, wherein aroma associated with the fluid is sensed by a user; and a case including a plurality of retaining areas 54, each one of the plurality of retaining areas 54 shaped complementary to each one of the plurality of devices 10, and one device 10 stored in one retaining area 54 when the device 10 is not in use. In kit 50, the scented fluid 34 includes scent additives and additionally comprises one or more of the following: (i) glycerin, (ii) propylene glycol, and (iii) a mixture of glycerin and propylene glycol.

As depicted in FIG. 6 and FIG. 6A, device 10A includes a lip 60 extending radially outward from annular surface 33 relative to vertical centerline extending through the center of one of the inserts. Here, centerline 64 is shown with reference to insert 28.

A first radius distance R1 of insert 28 is measured from centerline 64 to annular surface 33. A second radius distance R2 is measured from centerline 64 to a terminal lip end 66 of lip 60. A third radius R3 is measured from centerline 64 to inner surface 35. The lip 60 extends radially outward from the annular surface 33 on the insert 28 and terminating at a lip end 66 radially inward relative to the inner surface 35 of the cylindrical housing. Lip 60 includes an upwardly facing convex surface 70 above an imaginary horizontal midline 74 and a downwardly facing convex surface 72 below the midline 74 when viewed in cross section.

A first neck 68 is defined between terminal lip end 66 and inner surface 25 on cylindrical housing 12. The width of first neck 68 is less than that of well 13 measured between annular surface 33 and inner surface 35 below lip 60. This provides an advantage of a narrow passageway to discourage scented fluid 34 from flowing out of well 13 in the event device 10, 10A is placed on its side. Additionally a second neck exists in second cylinder 24 similar to the first neck 68 described above.

In one particular embodiment, the width of first neck 68 is in a range from about 0.01, 0.025, or 0.1 mm to about 0.1, 0.25, 0.5, 1, or 2 mm. While well 13 has a width from about 0.1, 0.25, or 0.5 mm to about 1, 2, or 3 mm. In one particular embodiment, first neck 68 has a width that is half the width of well 13 measured between annular surface 33 and inner surface 35 below lip 60.

Device 10A may further include a heating element 90. Heating element 90 may be battery powered and be rechargeable utilizing battery technology currently available in other e-cigarettes or fluid vaporizers. In one particular embodiment, heating element 90 is an electric-resistive heater positioned within the body of each one of the cylinders 22, 24. FIG. 6 depicts heating element 90 entirely beneath the well 13 (when viewed in cross section) within cylinder 22 and heats the aromatic fluid 34 from below. However, it is entirely possible to have a resistive heating element 90A that extends vertically upward from the bottom of well 13 within the body of cylinders 22, 24. For example, a coil resistive heating element 90A is shown and including an outer coil 92 and an inner coil 94 would around the walls defining well 13, wherein outer coil 92 is radially outward of well 13 relative to center 64 and inner coil 94 is inward of well 13 relative to center 64. Either one of the heating elements 90 or 90A are advantageous to device(s) 10, 10A because heating up the walls defining well 13 to thereby impart heat to fluid 34 makes the aroma/scent associated with said fluid richer/stronger than the fluid would be at room temperature.

In accordance with one aspect of the present invention, device 10, 10A releases therapeutic aromas or scents for inhalation by a user. The therapeutic aromas may have advantages and benefits such as reducing appetite as a person is attempting to quit smoking cigarettes, or such as encouraging the pleasant enjoyment of soothing aromas.

In operation, device(s) 10, 10A is provided to a user in a fully constructed form from a supplier in accordance with the embodiments described above. A user fills the annular well 13 with a scented fluid 34. One exemplary commercially available scented fluid 34 is available for sale ordinarily used in an electronic cigarette. The user grasps the housing 12 with the top surface 14 facing upwardly to expose the opening to the annular well 13. An amount of the scented fluid 34 is poured into the well 13. In one particular embodiment, the amount of fluid 34 in the well 13 does not rise above the top surface 32 of the insert 28, 30 when device 10 is placed with its top surface facing upwardly. Once well 13 is filled with fluid 34, the device 10 may be packed into a kit 50 for later use, or attached to the mouthpiece 36.

In operation and with respect to device 10A, once the well 13 is filled with fluid, the lip 60 limits and discourages fluid 34 from exiting well 13 in the event device 10A is laid on its side. The narrow neck 68 enables the surface tension of fluid 34 to remain high over the neck width as opposed to the amount of surface tension spanning the width of well 13 in device 10. The well 13 in device 10A has a non-uniform width inasmuch as the neck 68 is about half as wide and the well portion beneath lip 60.

In operation, once device 10 has been loaded or filled with fluid 34 in the non-limiting manner described above, device 10 is extracted from the retention area 54 in the kit container 50. The device 10 is then connected to the mouthpiece 36 via the magnet 38 to the bottom surface 16 on the mouthpiece 36. The first end 40 of mouthpiece 36 is moved towards the user's mouth 44 and nose 46. In one particular embodiment, the user places the first end 40 into their mouth 44.

With the first end 40 in the user's mouth 44, the device 10 is positioned slightly beneath the nostrils 48 at an angle complementary to the user's upper lip. The user then inhales through their mouth and nose simultaneously, or at least as simultaneously as possible, to get the full effect of the scent. Stated otherwise, the scent of the fluid affects the human sense of smell stronger when a person tries to inhale through their mouth and nose at the same time.

In some instances, the user may turn on heating element 90 or 90A to warm the aromatic fluid 34 prior to inhalation. The warming of fluid 34 create a stronger scent than if the fluid was placed in device 10 (or device 10A) at room temperature. Preferably, heating element 90 or 90A may be coupled to temperature control logic to regulate the temperature to which fluid 34 is heated. The purpose of the control logic is ensure the fluid is not heated beyond its boiling point which would lead to the fluid evaporating from the well 13. "Logic", as used herein, includes but is not limited to hardware, firmware, software and/or combinations of each to perform a function(s) or an action(s), and/or to cause a function or action from another logic, method, and/or system. For example, based on a desired application or needs, the temperature control logic may include a software controlled microprocessor, discrete logic like a processor (e.g., microprocessor), an application specific integrated circuit (ASIC), a programmed logic device, a memory device containing instructions, an electric device having a memory, or the like. The temperature control logic may include one or more gates, combinations of gates, or other circuit components. The logic may also be fully embodied as software. Where multiple logics are described, it may be possible to incorporate the multiple logics into one physical logic. Similarly, where a single logic is described, it may be possible to distribute that single logic between multiple physical logics.

After usage, device 10 is placed back into the respective compartment in kit 50. Another advantage of device 10 filled with fluid 34 is that fluid 34 will not leak out the top of device 10 if placed on its side. When device 10 is laid on its side, fluid 34 may extend beyond top of surface 32 of the insert 28, 30 due to gravitational forces, but fluid 34 will not leak out and is contained by the edge of top surface 14.

One exemplary method of use of device 10 or 10A may include the steps of: providing a housing 12 including a first member (i.e., first cylinder 22) having an inner surface 35, an first insert 28 smaller than the first member and positioned inward from the inner surface 35, the first insert 28 having an outer surface 33, and a first aromatic fluid well 13 formed between the inner surface 35 of the first member and the outer surface 33 of the first insert 28; filling the aromatic fluid well 13 a scented fluid 34; and positioning the housing 12 beneath nostrils 48 on a user, wherein scent from the scented fluid 34 is sensed by a user. This method may further include the step of: discouraging the scented fluid 34 from flowing out of the fluid well 13 when the housing is positioned such that a top surface 14 of the first member is not facing directly vertical (FIG. 1 and FIG. 2). Wherein the step of discouraging may be accomplished by a lip 60 extending radially outward from the outer surface 33 of the first insert 28 towards the inner surface 35 of the first member and terminating at a lip end 66; wherein a neck section 68 is defined between the lip end 66 and the inner surface 35 of the first member, the neck section 68 having a width less than that of the aromatic fluid well. Further, this exemplary method may include wherein the step of positioning the housing beneath nostrils 48 is accomplished by attaching the housing 12 to a mouthpiece 36, selectively and repeatably, wherein the mouthpiece 36 is held in place by a user mouth 44.

Alternative embodiments of the present invention are also herein contemplated by way of non-limiting example. In one particular alternative embodiment, device 10 may be in fluid communication with a separate fluid source connected via tubing and a pump. The pump may be electronically controlled to initiate the flow of scented fluid 34 to device 10. The electronic control may include a bank of scented fluids 34 for the operator to choose from. There also may be a plurality of levers or valves to selectively open or close a desired scent 34 from a source in either a manual or electronic manner.

Another alterative embodiment may provide a device 10 retaining a scented fluid 34 mixed with a gel in the annular well. In this embodiment, scented fluid mixed with a pectin gel, similar to Sure-Jell® commercially available for sale by Kraft foods. The gel increases the viscosity of the mixture to ensure it remains in the annular well.

Another alternative embodiment of the present invention provides a housing 12 contained in the mouthpiece 36 for convenient travel. This alternative embodiment provides a hollow storage container within the body of the mouthpiece 36 that is selectively opened by a user to reveal the device stored inside. The user then connects the housing to the outside of mouthpiece 36 as shown in FIG. 1, and then the user may store the device 10 inside the mouthpiece 36 when finished.

Yet another alternative embodiment may include scented fluid 34 stored within a cavity inside mouthpiece 36. In this instance, tubing may exist to draw the stored fluid 34 to the annular wells 13 on device 10. Further, tubing may extend to the first end 40 of mouthpiece 36 so that the user may inhale simultaneously through the user's nose and mouth in accordance with the techniques described herein.

Another non-limiting alternative embodiment may include a tube bifurcating to create a generally Y-shaped member acting as the mouthpiece. Around the tube there may be layers of scents in compartments housed adjacent the tube. The tube may define a plurality of holes for attaching the scent compartments there around. Each scent compartment could have a small device 10 to keep the fluid 34 from leaking out. Each compartment may have a sliding door. Because the device 10 in this alternative embodiment may be smaller than in the embodiments described above, annular well 13 would contain about 1-3 drops of fluid 34. All of the sliding doors could be connected by a sturdy, thin cord so when a user pulls on a lever operatively connected to a desired scent located outside of the device 10, the cover then closes other doors so the other scents would be pulled tightly shut. Thus, in this embodiment there will be one scent door open all the time. The aroma from a scented fluid located adjacent an open door will enter into the aperture of the tube flowing upwardly to the generally Y-shaped mouth piece. Additionally, there may be an instance where two or more of these scent containers are open at a single time, allowing the aromas to mix in the container outside the device then collectively flow through the apertures at the lower end of the tube towards the Y-shaped mouthpiece.

Another non-limiting alternative embodiment may include a headset-like device electronically controlled by a remote control to change the scents. The headset is donned by a user such that it wraps around the user's head to free up the user's hands to perform another task. The headset may be configured with a device 10 retaining area positioned adjacent the user's nose when the headset is donned.

Top surface 32 is depicted throughout the figures as a flat horizontal surface when viewed in cross section, however it is possible that top surface 32 be arcuate, either convexly or concavely. Further, future embodiments may include a concave top surface bowing downwardly to define a second well radially inward (i.e., towards the center) relative to well 13. This may prove advantageous to mix scents without actually mixing fluids.

Further, for brevity, it is to be understood that the second cylinder 24 having second insert 30 includes the same features described above and reference numerals have similar meanings with respect to each left and right (first and second) cylinder 22, 24. Namely, devices 10 and 10A include a second cylinder having an inner surface, the second cylinder defining another portion of the housing; a second insert having an outer surface, the second insert smaller than the second cylinder and positioned radially inward from the inner surface; and a second aromatic fluid well formed between the inner surface of the second cylinder and the outer surface of the second insert configured to retain a scented fluid therein, wherein aroma associated with the fluid is inhaled by a user. The first cylinder 22 and the second cylinder 24 are linearly aligned for positioning directly beneath two nostrils of the user when viewed from above (FIG. 3).

Figure 7:
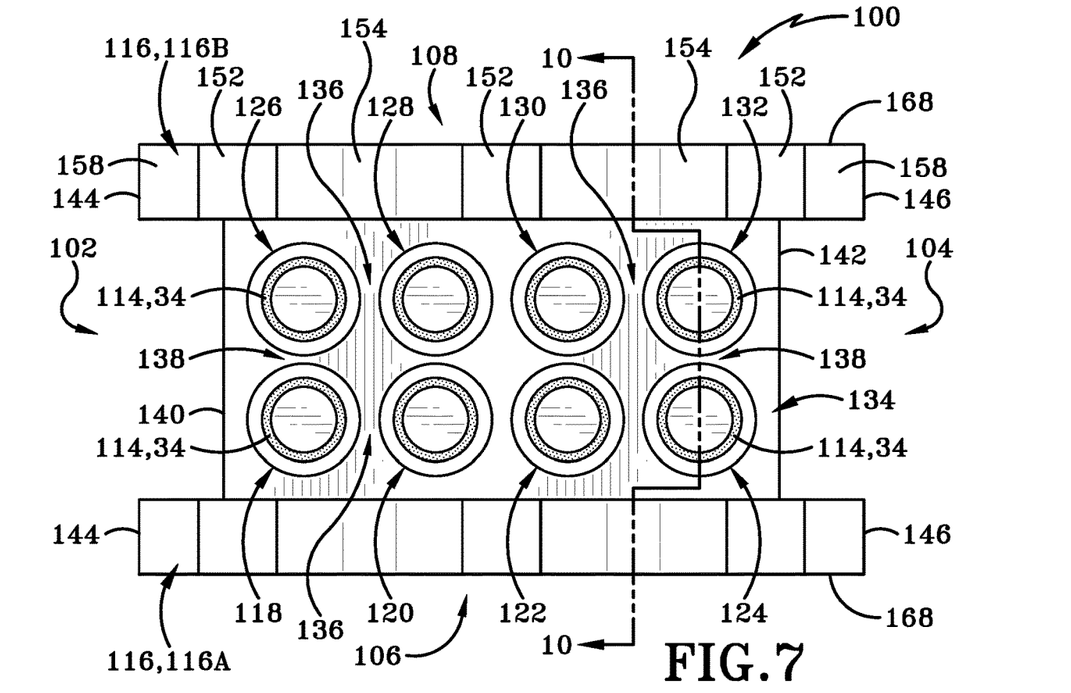
FIG. 7 is a top plan view of an alternative embodiment of an aromatherapy device in accordance with the present disclosure.

FIG. 7 depicts an alternative embodiment of an aromatherapy device in accordance with the present disclosure generally at 100. Device 100 includes a first end 102 opposite a second end 104 defining a longitudinal direction therebetween. Device 100 includes a first side 106 opposite a second side 108 defining a transverse direction therebetween. Device 10 includes a top 110 opposite a bottom 112 defining a vertical direction therebetween. Device 100 may generally be formed as a unibody monolithic member having a variety of components formed therein, some of which are described below. However, it should be noted that while some of the components discussed below are may be constructed or formed from a uniform material, similar components accomplished similar objected could be assembled from discrete or independent components.

With continued reference to FIG. 7-FIG. 10, device 100 may include a plurality of wells 114 formed in upper portion of the device and a plurality of wells 114 formed in a lower portion of the device. In one particular embodiment, the plurality of annular wells 114 may be located transversely between parallel side members 116 which may also act as a mouthpiece or nose guard or lip guard during the inhalation of scent/aroma of the fluid 34 stored in the plurality of annular wells 114. In one particular embodiment, device 100 is considered to be dual sided inasmuch as the annular wells 114 are provided in the top portion of the device and provided in the bottom portion of the device. The wells 114 may be filled and carry fluid at the same time so as to allow the device 100 to be flipped over or rotated 180° about at a longitudinal axis or a transverse axis so as to allow a user to vary the scents that are inhaled.

In one particular embodiment, device 100 may include at least four pairs of annular wells 114. More particularly, the at least four pairs of annular wells are located on the same side of the device and face one similar direction (such as up or down). Further, a first pair of annular wells may be respectively defined by a first cylinder 118 and a second cylinder 120. A second pair of annular wells may be respectively defined by a third cylinder 122 and a fourth cylinder 124. A third pair of annular wells 114 may be respectively defined by a fifth cylinder 126 and a sixth cylinder 128. A fourth pair of annular wells may be respectively defined by a seventh cylinder 130 and an eighth cylinder 132. Each of the cylinders 118, 120, 122, 124, 126, 128, 130, and 132 are connected with a central portion 134 that extends transversely between the side members 116. Additionally, while the wells 114 are described and identified as being annular in shape, they may be formed in other shapes. In one particular embodiment, the central portion 134 and the cylinders 118, 120, 122, 124, 126, 128, 130, and 132 are integrally molded together.

The first cylinder 118 is longitudinally aligned with the second cylinder 120 and associated with the first side 106 of device 100. The third cylinder 122 and the fourth cylinder 124 are longitudinally aligned with the first and second cylinders 118, 120. The third and fourth cylinders 122, 124 are associated with the first side 106 of device 100. The fifth cylinder 126 and the sixth cylinder 128 are longitudinally aligned and associated with the second side 108 of the device 100. Stated otherwise, the first cylinder 118 and the fifth cylinder 126 are transversely aligned. The second cylinder 120 and the sixth cylinder 128 are transversely aligned. The seventh cylinder 30 and the eighth cylinder 132 are longitudinally aligned with the fifth cylinder and sixth cylinder 126, 128. The seventh cylinder 130 is transversely aligned with the third cylinder 122 and the eighth cylinder 132 is transversely aligned with the fourth cylinder 124. The spacing between adjacent cylinders is a distance that would effectuate the positioning of respective cylinders beneath two nostrils of the user. For example, the space 136 defined between the first cylinder 118 and the second cylinder 120 is equal to or approximates the space between two nostrils on a user's nose. In one particular embodiment, this may be on the order of a few to multiple millimeters, such as 1 millimeter to about 30 millimeters. Additionally, a longitudinally extending gap 138 may be defined between the first through fourth cylinders and the fifth through eighth cylinders. Gap 138 may be transversely centered along the longitudinal axis of the device 100 so as to approximate a central plane extending longitudinally from the first end 102 to the second end 104. In one particular embodiment, gap 138 is smaller in dimension than the gap 136. However, it is entirely possible that other design configurations are envisioned where the gap 138 has a similar dimension as the gap 136 or a larger dimension than the gap 136.

Each of the cylinders 118, 120, 122, 124, 126, 128, 130, and 132 extends upwardly from the surface of the central portion 134. Central portion 134 includes a first end wall 140 and a second end wall 142, each of which extends transversely between the side members 116. The first end wall 140 is not coplanar with the terminal ends or the forward ends of the side members 116. However, it is envisioned that other embodiments of device 100 could provide a scenario where the central portion 134 includes a first end wall 140 coplanar with the terminal ends of the side members 116. Similarly, the second end wall 142 terminates short from the terminal ends of the second end of the side members 116 such that the second end wall 142 is not coplanar with the second terminal ends of the side members 116. However, it is also similarly envisioned that a device may be manufactured which would provide an end wall 142 that is coplanar with the terminal ends of the side members 116. However, it is envisioned that the central portion 134 may be thickened and the annular wells 114 may be formed by a central portion 134. In this case, the cylinders would not need to extend upwardly. Rather, the wells would simply be counter sunk into the thickened central portion.

Cylinders 118, 120, 122, 124, 126, 128, 130, and 132 may be similarly sized and shape such that each respective annular well has similar dimensions, such as depth and diameter (both inner diameter and outer diameter) as the other wells. However, it should be understood that there may instances where it would be advantageous to create cylinders or wells having varying sizes. This could effectuate the carrying of fluid 34 that has varying viscosities. For example, a more viscous fluid 34 could be carried in a wider annular well (i.e., wider referring the space between the inner diameter and the outer diameter, such as the distance between wall 160 and wall 164).

With continued reference to FIG. 7, the transverse spacing between side members 116 is greater than about two times the diameter of one respective cylinder. Stated otherwise, two cylinders are aligned transversely between the side members 116. Accordingly, the transverse width of the central portion 134 must accommodate two cylinders transversely aligned. In one particular embodiment, when there are eight cylinders that face upwardly from the upwardly facing first surface of the central portion 134, the eight cylinders 118, 120, 122, 124, 126, 128, 130, and 132 are arranged in a 2×4 array. In one particular embodiment, the array is at least a 2×2 array.

In one particular embodiment, there may be two side members 116A, 116B. First side member 116A is associated with the first side 106 and the second side member 116B is associated with the second side 108. Each of the side members 116A, 116B includes a forward terminal end 144 and a second terminal end 146. Each side member 116 includes an upwardly facing first surface 148 and an opposing downwardly facing second surface 150. In one particular embodiment, the first surface 148 and the second surface 150 are mirror opposites of each other. The surfaces 148, 150 may be formed with a plurality of planar or flat portions 152 and a plurality of intermediate arcuate sections 154 in between or interposed between adjacent flat portions 152. A flat portion 152 on the top surface 148 may be directly vertically aligned with a flat portion 152 on the bottom surface 150. The flat portions 152 form the thickest or greatest vertical distance of the side members 116. This may also be referred to as a thickened dimension. This thickened dimension of the side members 116 may be greater than a maximum vertical dimension associated with the wells 114 or any of the cylinders arranged top-to-bottom (i.e., the top of cylinder 132 to the bottom of cylinder 132'). This allows the device to be laid upside down and precludes the cylinders from contacting the supporting surface. Similarly, the arcuate sections 154 on the top surface 148 may be directly vertically aligned with the arcuate sections 154 on the bottom surface 150. The cutout arcuate sections 154 may form the narrowest portion of the side member 116. In one particular embodiment, the arcuate cutout sections 154 are defined by concave edges. In other embodiments, the sections 154 do not need to be arcuate, rather they may be any shape that effectuates a narrowed dimension or narrowed vertical height of the side members 116. Additionally, it is entirely possible for an end concave arcuate section 158 to connect with respective terminal ends 144, 146. Additionally, the side members 116A, 116B may be integrally formed with the central portion 134 when the device 100 is fabricated from a single uniform material (as shown in cross section in FIG. 10).

Figure 8:
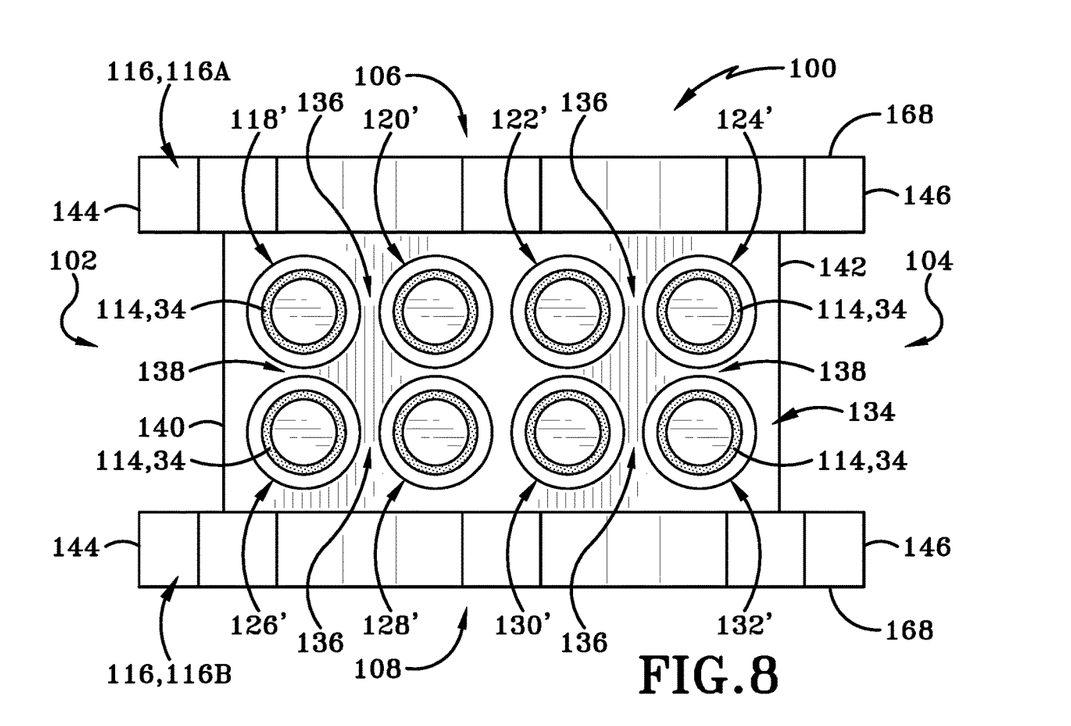
FIG. 8 is a bottom plan view of the alternative embodiment of the aromatherapy device.
Figure 9:
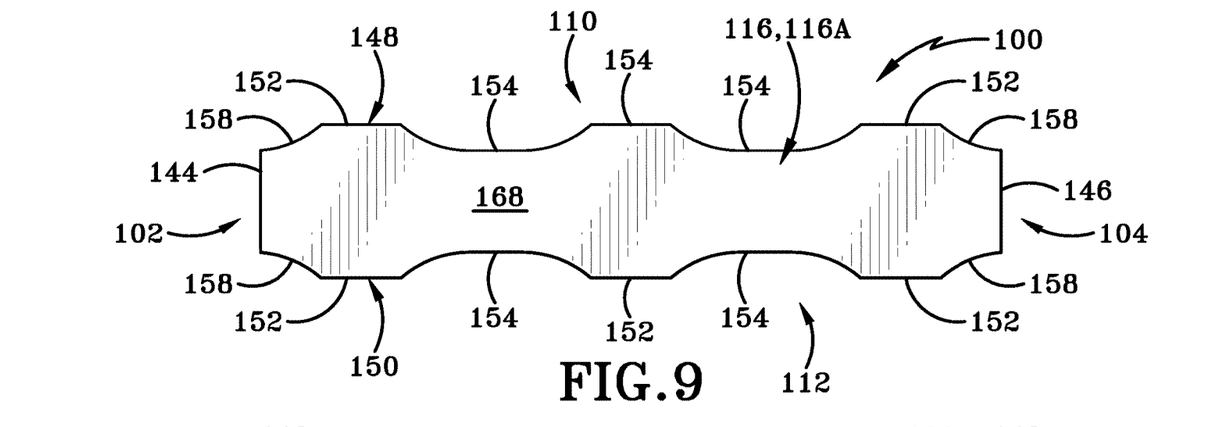
FIG. 9 is a side elevation view of the alternative embodiment of the aromatherapy device.

FIG. 8 depicts a plurality of bottom annual wells 114 positioned on the bottom of the central portion 134. Similar to the top position of the device 100, the bottom portion of the device forms eight annular wells which may be defined by eight cylinders that mirror the eight cylinders formed in the top portion of the device. Particularly, there may be a bottom first cylinder 118', a bottom second cylinder 120', a bottom third cylinder 122', a bottom fourth cylinder 124', a bottom fifth cylinder 126', a bottom sixth cylinder 128', a bottom seventh cylinder 130', and a bottom eighth 132'. Bottom cylinders 118'-132' are formed similar as the top cylinders 118-132, but face in the opposite direction.

Figure 10:
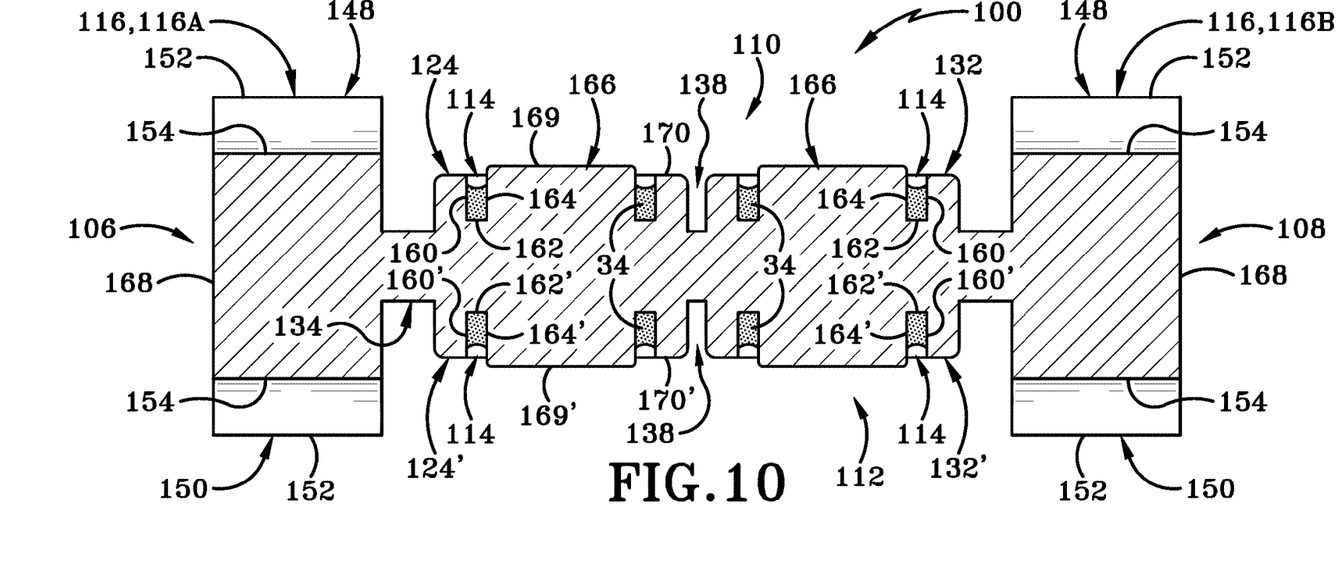
FIG. 10 is a cross-section view taken along line 10-10 in FIG. 7.

As depicted in FIG. 10, each annular well 114 defined by each respective cylinder may be formed from a first cylindrical wall 160 connected with a bottom wall 162 which is connected with a second cylindrical wall 164 on a center region 166 which may also be referred generally to as an insert 166. Similar walls may be formed on the bottom cylinder and are identified by prime numerals, such as wall 160', wall 162', and wall 164'. In each instance, annular well 114 on the upper cylinder 124 or the other upper cylinders aligns directly above the bottom respective cylinder 124' or other respective bottom cylinders. Similar to the other embodiments, the height of the insert 166 may be similar to that of the height of the outer portion of the cylinder or it may be below the height of the outer portion of the cylinder as detailed in FIGS. 1-6. However, as detailed in FIG. 10, the insert 166 may have a flat surface 169 that is vertically higher than the top portion 170 of an outer annular portion of the cylinder 124.

With continued reference to FIG. 10, the aromatic or scented fluid 34 deposited in each annual well 114 includes a scent as described above with respect to the other embodiments. In one particular embodiment, based on the small dimensions of the well 114, the viscosity of the fluid 34 may be similar to that of water. However, other embodiments may provide a thicker viscosity fluid 34 including artificial flavors to effect the scent and other components or substances, such as propylene glycol or glycerin. In each instance, viscosity of the fluid is a sufficient value to prevent the fluid 34 from leaking out of the well 114 when the device 100 is placed upside down. Stated otherwise, the device 100 is configured to rest on the flat portions 152 of the side members 116. When resting on the flat portions 152, at least two wells 114 will face downwardly. Thus, the effect of gravity will pull on the fluid 34 in the downwardly facing wells 114. However, the viscosity of the fluid 34 is of a sufficient value to substantially adhere to the walls 160, 162, and 164 (or, respectively, 160', 162', and 164') to prevent the fluid from leaking out of the well 114. State otherwise, the fluid 34 disposed in the annular wells 114 has a viscosity value that is greater than gravitational forces attempting to pull the fluid 34 out of the well 114.

Figure 11:
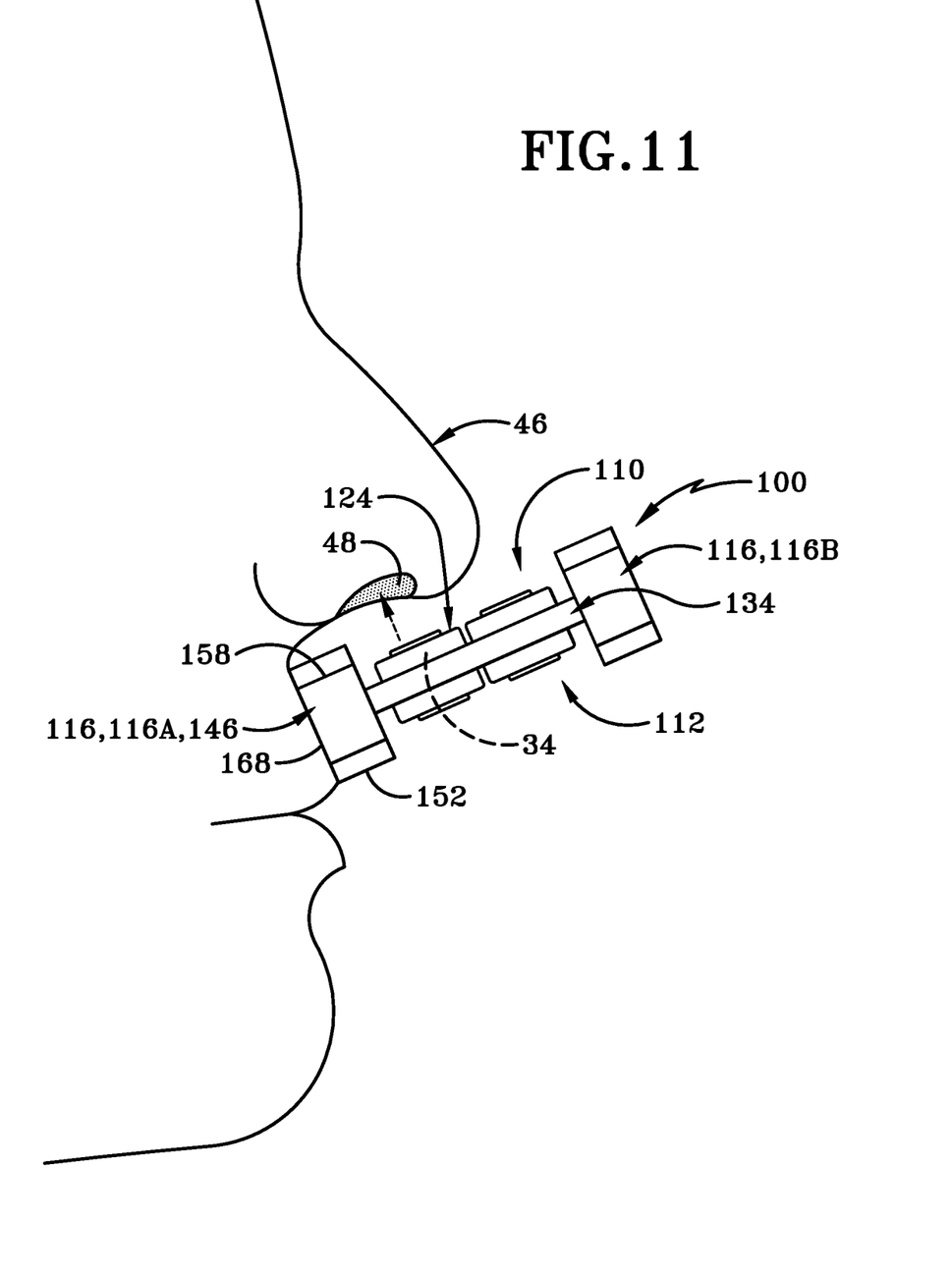
FIG. 11 is an operational side view of the alternative embodiment of the aromatherapy device.

In operation and with reference to FIG. 11, the user will fill respective pairs of wells with scented fluid 34. In one particular embodiment, there are eight pairs of wells (four pairs on the top and four pairs on the bottom defined by sixteen cylinders total). Each pair of wells 114 should be filled with a fluid, which may vary in scent, such that they may be positioned beneath the nostrils 48 of the user 46. A vertical sidewall 168 on the side members 116 may be positioned closely adjacent the user's upper lip so as to act as a mouthpiece or lip guard or an alignment guard or a lip rest such that user can inhale the scent of the fluid 34 disposed within each well 114. For example, a user may fill the first and second cylinders 118, 120 (i.e., the first pair) with a similar scented fluid. Then, the user can fill the second pair of annular wells 114 formed from the third and fourth cylinders 122, 124 with a different second scent. The user may repeat this process until all eight pairs (16 cylinders) are filled with the scents that the user desires. In use, the operator will position adjacent pairs of annular wells holding the scented fluid beneath the nostrils 48. The user may manipulate and maneuver the device 100 so as to be able to exploit the advantages of the aromatherapy device 100 by installing up to eight different scented pairs of annular wells 114.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims (if at all), should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

An embodiment is an implementation or example of the present disclosure. Reference in the specification to "an embodiment," "one embodiment," "some embodiments," "one particular embodiment," or "other embodiments," or the like, means that a particular feature, structure, or characteristic described in connection with the embodiments is included in at least some embodiments, but not necessarily all embodiments, of the invention. The various appearances "an embodiment," "one embodiment," "some embodiments," "one particular embodiment," or "other embodiments," or the like, are not necessarily all referring to the same embodiments.

If this specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

Additionally, any method of performing the present disclosure may occur in a sequence different than those described herein. Accordingly, no sequence of the method should be read as a limitation unless explicitly stated. It is recognizable that performing some of the steps of the method in a different order could achieve a similar result.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

What is claimed:

1. An aromatherapy device comprising:
a plurality of distinct open annular wells arranged in an array and spaced apart and adapted to be positioned beneath two respective nostrils for inhalation of a scent from a fluid at least partially filling the two adjacent and distinct open annular wells, wherein the distinct open annular wells are defined by an outer wall, a lower wall, and an inner wall;
a first open annular well from the plurality of distinct open annular wells that is aligned with a second open annular well from the plurality of distinct open annular wells; and
a third open annular well from the plurality of distinct open annular wells that is aligned with a fourth open annular well from the plurality of distinct open annular wells;
a fifth open annular well from the plurality of distinct open annular wells that is aligned with a sixth open annular well from the plurality of distinct open annular wells;
a seventh open annular well from the plurality of distinct open annular wells that is aligned with an eighth open annular well from the plurality of distinct open annular wells; and
an additional eight bottom downwardly open annular wells from the plurality of distinct open annular wells arranged in a mirrored configuration as the first through eighth open annular wells to collectively define at least sixteen open annular wells from the plurality of distinct open annular wells.

2. The aromatherapy device of claim 1, wherein the first and second open annular wells are longitudinally aligned with the third and fourth open annular wells.

3. The aromatherapy device of claim 1, wherein the first and second open annular wells are transversely aligned with the third and fourth open annular wells.

4. The aromatherapy device of claim 1, wherein the first and second open annular wells are vertically aligned with the third and fourth open annular wells.

5. The aromatherapy device of claim 1, further comprising:
a pair of longitudinally extending side members, wherein the first through fourth open annular wells are disposed between the pair of side members, and a thickened dimension of the pair of side member greater than a maximum vertical dimension of the first through fourth open annular wells.

6. The aromatherapy device of claim 5, wherein at least one side member from the pair of side members includes:
a flat portion connected with an arcuate section, wherein the thickened dimension is measured through the flat portion.

7. The aromatherapy device of claim 6, further comprising a central portion extending transversely between the pair of side members.

8. The aromatherapy device of claim 7, further comprising:
a first cylinder carried by the central portion and defining the first open annular well;
a second cylinder carried by the central portion and defining the second open annular well;
a third cylinder carried by the central portion and defining the third open annular well; and
a fourth cylinder carried by the central portion and defining the fourth open annular well.

9. The aromatherapy device of claim 8, further comprising:
a first gap defined between the first cylinder and the second cylinder, wherein the dimension of the first gap is from 1 millimeter to 30 millimeters.

10. The aromatherapy device of claim 9, further comprising:
a fifth cylinder carried by the central portion and defining the fifth open annular well;
a sixth cylinder carried by the central portion and defining the sixth open annular well;
a seventh cylinder carried by the central portion and defining the seventh open annular well; and
an eighth cylinder carried by the central portion and defining the eighth open annular well.

11. The aromatherapy device of claim 1, further comprising a central portion integrally forming the plurality of open annular wells.

12. The aromatherapy device of claim 1, wherein the array is at least a 2×2 array.

13. An aromatherapy device defining a plurality of annular wells arranged in an array adapted to be filled with fluid as scented pairs for two adjacent wells positioned beneath nostrils while resting a portion of the aromatherapy device near an upper lip, the annular wells formed by respective inner and outer cylindrical walls and a lower wall, wherein a first plurality of at least eight wells face a first direction and a second plurality of at least eight wells face an opposite second direction, wherein the wells are sized to receive fluid therein having different scents associated therewith, and a viscosity of the fluid is sufficient to preclude gravity from effecting the fluid to flow out of the wells when the aromatherapy device is positioned upside down and some of the wells are, at least temporarily, downwardly facing.

14. An aromatherapy device comprising:
a plurality of distinct open annular wells arranged in an array of columns and rows, wherein the distinct open annular wells are defined by an outer wall, a lower wall, and an inner wall;
a first open annular well from the plurality of distinct open annular wells that is longitudinally aligned with a second open annular well from the plurality of distinct open annular wells;
a third open annular well from the plurality of distinct open annular wells that is longitudinally aligned with a fourth open annular well from the plurality of distinct open annular wells,
a fifth open annular well from the plurality of distinct open annular wells and a sixth open annular well from the plurality of distinct open annular wells;
a seventh open annular well from the plurality of distinct open annular wells and an eighth open annular well from the plurality of distinct open annular wells;
wherein the first through eighth open annular wells are all upper annular wells from the plurality of distinct open annular wells; and
an additional eight bottom downwardly open annular wells from the plurality of distinct open annular wells arranged in a mirrored configuration as the upper annular wells to collectively define sixteen open annular wells from the plurality of distinct open annular wells.

* * * * *